United States Patent
Ramadoss et al.

(10) Patent No.: US 6,264,998 B1
(45) Date of Patent: Jul. 24, 2001

(54) EXTRACTING BETULINIC ACID FROM ZIZIPHUS JUJUBA

(75) Inventors: Sunder Ramadoss, New Delhi; Mohammad Jamshed Ahmed Siddiqui, Delhi, both of (IN)

(73) Assignee: Dabur Research Foundation, Ghaziabad (IN)

( * ) Notice: Subject to any disclaimer, the term of this patent is extended or adjusted under 35 U.S.C. 154(b) by 0 days.

(21) Appl. No.: 09/516,032

(22) Filed: Mar. 1, 2000

(51) Int. Cl.$^7$ ...................................................... A61K 35/78
(52) U.S. Cl. ............................................. 424/775; 424/725
(58) Field of Search ...................................... 424/775, 725

(56) References Cited

U.S. PATENT DOCUMENTS 5,589,182 * 12/1996 Tashiro et al. ........................ 424/423
6,048,847 * 4/2000 Ramadoss et al. ................... 514/169
6,175,035 * 1/2001 Draeger et al. ....................... 560/116

OTHER PUBLICATIONS

Schuhly et al., Planta Medica, 65, 1999, 740–743.*

* cited by examiner

Primary Examiner—David M. Naff
Assistant Examiner—Mike Meller
(74) Attorney, Agent, or Firm—Ladas & Parry

(57) ABSTRACT

A process for isolating betulinic acid from *Ziziphus jujuba* is disclosed. The process involves the steps of:
a) extracting bark of *Ziziphus jujuba* in a solvent to obtain an extract containing betulinic acid,
b) semi-concentrating the extract containing betulinic acid,
c) chilling said semi-concentrated extract overnight to obtain a solid in the extract,
d) separating the solid from the extract by filtration or centrifugation,
e) dissolving the separated solid from step d) in hot methanol, refluxing with activated charcoal and filtering through a celite bed to obtain a methanolic solution,
f) partially concentrating the methanolic solution of step e), adding halogenated hydrocarbon solvent and chilling overnight to obtain a solid in the solution,
g) separating the solid of step f) by filtration or centrifugation and drying the solid to obtain a solid enriched in betulinic acid,
h) dissolving the dried solid step g) in a solvent containing pyridine and acetic anhydride, separating an organic layer and drying to obtain a crude 3-acetoxy betulinic acid,
i) washing the crude solid 3-acetoxy betulinic acid obtained in step h) with an alcohol to yield pure solid 3-acetoxy betulinic acid obtained in step i) in an aqueous alcoholic alkali solution to yield pure betulinic acid.

13 Claims, 1 Drawing Sheet

EXTRACTING BETULINIC ACID FROM ZIZIPHUS JUJUBA

FIELD

Figure 1:
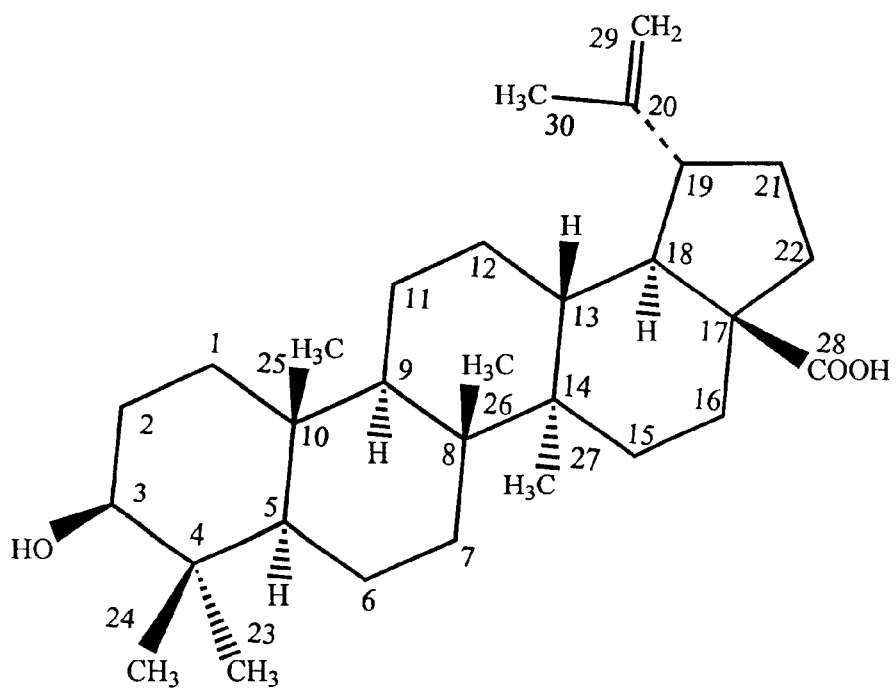

The present invention relates to the field of phytochemistry. More specifically, the invention provides a simple and cost effective method for the isolation of betulinic acid from the bark of Ziziphus jujuba.

BACKGROUND

Under the auspices of National Cooperative Natural Product Drug Discovery group supported by National Cancer Institute, the potential antitumor activity of approximately 2500 extracts derived from globally collected plants was evaluated. One such extract, prepared from stem bark of Ziziphus mauritiana Lam (Rhamnaceae) displayed selective cytotoxicity against cultured human melanoma cells (National Medicine, Vol.1(10), 1995, No.96/29068). The active principle responsible was identified as betulinic acid, whose structure is represented in FIG. 1 of the accompanying drawings. This prompted the applicants to devise a process for the isolation of betulinic acid from the bark of Ziziphus jujuba which is abundantly available in India.

The compound betulinic acid has been isolated mainly from bark, seed, kernels and leaves of various plants. The extraction of biomass with methanol, chloroform, benzene or ethereal solvent yielded an extract which is treated with alkaline solution to selectively extract acidic components, which is subsequently methylated and the product chromatographed to yield methylester of betulinic acid. Unfortunately, since benzene is highly carcinogenic, this method was abandoned. Some of the common methods employed in the art for the extraction of betulinic acid are given herein below.

Alpin et. al. Chemistry of Titerpenes and related compounds, Part XLIII p3269, relates to extraction of betulinic acid from the bark of Platanus x hybrida Brot. In this process, the bark was extracted with methanol and partly evaporated, whereupon betulinic acid was crystallized. The ether-soluble portion of the remaining material was separated into neutral and acidic fractions. From the acidic fraction, some more betulinic acid was isolated as methylester by treatment with diazomethane followed by column chromatography. Unfortunately, this method involves hazardous steps and reagents such as methylating with ethereal diazomethane; accordingly, this process was found to be unfit for commercial exploitation.

Current Science, 1965, p.344, relates to extraction of bark of ziziphus jujuba with light petroleum ether and ether solvent; followed by extraction of ether extract with sodium hydroxide solution thereby leading to the isolation of sparingly soluble sodium salt of betulinic acid. In this process extraction of organic layer with alkali solution leads to emulsion problems. Once emulsion is formed no discrete layer separation is obtained. Therefore, it is difficult to implement this process on commercial scale. In addition, this process also leads to wastage of the required compound involving cumbersome operational activities.

Phytochemistry, 1968, Vol.7, p461, relates to the extraction of seed kernels of Alangium lamarckii with light petroleum ether, benzene and chloroform respectively. The residue from benzene and chloroform extracts are poured onto ice water to yield a solid. The solid was dissolved in chloroform and extracted with 3% aqueous KOH. The precipitated potassium-salt was filtered, washed with water to free it from alkali. The K-salt was further treated with 2N HCl and extracted with ether. The ethereal solution was charcoalised in MeOH—CHCl$_3$ and followed by repeated crystallisation of the residue from methanol which finally yielded pure betulinic acid. Even in this process, it is impossible to get discrete layer separation and hence, this process is also unfit for commercial exploitation.

Aus. J. Chem., 1969, 22, p1331, relates to the extraction bark of Akania lucens (F. Muell) also known as "turnip wood", with light petroleum ether and methanol. The ether soluble portions of these extracts were separately worked by extracting with NaHCO$_3$, Na$_2$CO$_3$ and NaOH solution, followed by methylation of the residue obtained and purification by column chromatography to yield methylester of betulinic acid. It is apparent that this process is quite cumbersome and unfit for commercial exploitation. This process involves interface formation which is apparent from the citation.

Journal of Indian Chemical Society, 1969, Volume 46, No.4, p.386, relates to preparation of triterpenoids from the bark of Rhododendron arboreum. This process is tedious and involves the use of hazardous materials such as ethereal solution of diazomethane. The process is unfit for commercial production of betulinic acid.

Ind. J. of Chemistry (1972), p.152, deals with the isolation of betulinic acid from Ziziphus rugosa Lam. by extracting it with alcohol and obtaining concentrated alcoholic extract, which is further extracted with chloroform and filtered to remove the insoluble material. Chloroform soluble portion was evaporated to dryness, defatted with petroleum ether, followed by chromatography of the residue which yielded betulinic acid.

Prot. Nat. Acad. Sci. India, (1975), p.300, describes the extraction of plant Anemone rivularis with alcohol, followed by concentration and chilling of extract to give a brown residue which is digested with ether. The ether soluble portion was extracted with potassium hydroxide to yield potassium salt of betulinic acid. The above processes involve usage of ether which is hazardous. In addition, other disadvantages cited earlier such as performing chromatography are also associated with the processes.

Phytochemistry, 1970, Vol.9, p907, relates to the extraction of bark of Arbutus menziesii with methanol. The methanolic extract was treated with chloroform and the chloroform solution filtered through alumina and evaporated to yield a residue, which was further treated with methanol and acetic acid to yield a residue. This residue was again chromatographed on silica gel to yield betulinic acid. This process involves expensive and tedious steps of chromatography.

Filoterapia (1987), p.58, describes the isolation of betulinic acid from Zizyphus sativa by extraction of the stem bark of the plant with C$_6$H$_6$:MeOH:NH$_4$OH mixture in the ratio of 100:1:1 respectively. The basic compounds were separated from the extract by extraction with aqueous citric acid and benzene fraction left behind is evaporated to dryness and chromatographed on silica gel to yield betulinic acid.

Planta Medica, 1988, p.511, relates to the extraction of twig of Agrostistachys hookeri with chloroform, followed by column chromatography of the extract to yield betulinic acid. This involves expensive and tedious steps of chromatography.

J. Nat. products, 1994, Vol.57, p.243, relates to the extraction of leaves of Syzigium claviforum with methanol. The methanol extract was partitioned successively with hexane, chloroform, ethyl acetate and n-butanol. Betulinic acid was isolated by repeated column chromatography of chloroform soluble portion.

Chem. Pharm. Bull. (1996), p.1033, described isolation of betulinic acid from hot chloroform extract of outer bark of *Betula pentayphylla* var *japonica*. The extract is concentrated, added ethanol to crystallise crude betulin. The mother liquor was chromatographed to yield betulinic acid as one of the product.

Planta Medica 1997, p.255, describes the isolation of betulinic acid from root bark of *Triphyophyllum pelatum* and *Ancistrocladus heyneanus* by extracting with petroleum ether and chromatography of the residue obtained over silica gel.

Synthetic communications, 1997, p.1607, describes a method for synthetic conversion of betulin to betunic acid.

U.S. Pat. No. 5,804,575 relates to synthetic conversion of betulin (present to the extent of 25% W/W in the bark of white birch, *Betula alba*) to enantiomerically pure beta-isomer of betulinic acid). Since the above methods relate to synthetic conversion, they are no way related to the applicant's present process. The applicant's recently accepted U.S. patent application Ser. No. 09/040,856 dated Mar. 18, 1998 discloses a process for producing active betulinic acid analogues. This process involves altogether a different procedure.

The prior art mentioned above teaches the isolation of betulinic acid from biomass involving either tedious, costly procedure of involving chromatography or either practical difficulty of emulsion formation during the partition of extract with alkaline solutions like $NaHCO_3$, $Na_2CO_3$, NaOH and KOH. Here again, the step of methylation using diazomethane prior to column chromatography is used which is both expensive and hazardous to be implemented for commercial operation. Thus, all the prior art methods teaching extraction of betulinic acid from Ziziphus are cumbersome and not fit for commercial utilization.

To overcome these and other drawbacks of the methods in the prior art, the applicants have developed a novel process which is economical, ecofriendly, easy operational procedure and non-hazardous for the commercial isolation or manufacturing of betulinic acid with purity not less greater than 98%. Another feature of the present invention is to employ acylation to derive crude betulinic acid in the process for isolation of pure betulinic acid, which is easy, inexpensive and non-hazardous.

OBJECTS

Accordingly, the main objective of the present invention is to provide a simple and cost effective process for the extraction of betulinic acid which forms the basic molecule for the invention of new anticancer drug.

Another objective is to provide a process which does not involve tedious step of chromatographic technique at any stage for the isolation of betulinic acid.

Yet another objective is to provide a process wherein the solvent used in various steps can be recycled.

Still another objective is to provide an ecofriendly process which provides complete isolation of betulinic acid from the raw material used.

One more objective relates to a process which results in betulinic acid having purity greater than 98%.

SUMMARY

In accordance with the above and other objects, the present invention provides a novel process for isolation of betulinic acid from primary extract on a commercial scale from plant extract of *Ziziphus jujuba* by solvent crystallisation without employing chromatographic separation.

DETAILED DESCRIPTION

Accordingly, the invention provides a novel process for the isolation of betulinic acid on a commercial scale from plant extract of *Ziziphus jujuba,* said of bark of *Ziziphus jujuba,* concentration of extract to a definite volume, chilling, centrifuging or filtering separate the solid (I) and mother liquor. The solid (I) is charcoalised in methanol, methylene chloride is added and chilled. This is then filtered to separate solid (II) and acylated with $Py/Ac_2O$ to get a mixture of acylated product, which is purified by treatment with isopropanol to give pure 3β-acetoxy betulinic acid. The acetate is treated with methanolic aqueous alkaline solution to yield pure betulinic acid. FIG. 1 represents the structure of betulinic acid.

The invention provides a process for the isolation of betulinic acid from *Ziziphus jujuba,* said process comprising the steps of:

a) extracting the optionally dried and pulverized parts of *Ziziphus jujuba* in a solvent, b) preparing a semi-concentrated extract containing betulinic acid, c) chilling the concentrated extract overnight, d) separating the solid from the extract by filtration or centrifugation, e) charcoalising the solid obtained in step (d) with reflux methanol and filtering through celite bed, f) partially concentrating methanolic solution of step (e), adding halogenated hydrocarbon solvent and chilling overnight, g) separation of solid by filtration or centrifugation followed by drying, h) treating the solid of step (g) with $Py/Ac_2O$ to yield acetylated product, i) macerating the acetylated product obtained in step (h) with an alcohol to yield pure 3β-acetoxy betulinic acid, and j) treating the solid obtained in step (i) with aqueous alcohol-alkali solution to yield pure betulinic acid (3β).

In an embodiment, the solvent used for the preparation of extract of plants is selected from the group of aromatic hydrocarbons comprising benzene, toluene and xylene.

In another embodiment, the preferred solvent is toluene.

In yet another embodiment, the halogenated hydrocarbon solvent is methylene chloride.

In a further embodiment, the alcohol for washing the acetylated product is selected from methanol, ethanol and isopropanol, preferably isopropanol.

In still another embodiment, the semi-concentrated extract is chilled to yield crude betulinic acid.

In an embodiment, the preferred alcohol used in step (i) is isopropanol. In another preferred aspect of this invention, the chilling in steps (c) and (d) is performed between 0 to 10° C. and the partial concentration in step (f) is performed under reduced pressure.

In yet another embodiment, the alkali solution in step (j) is prepared in aqueous-alcoholic mixture.

In a further embodiment, the crude betulinic acid is crystallized from the methanol-methylene chloride mixture, preferably in the ratio 1:4.

In yet another embodiment, the crude betulinic acid is dissolved in the halogenated solvent containing organic base, preferably pyridine, and treating it with acylating agent, preferably acetic anhydride.

In an embodiment, the crude 3β-acetoxy betulinic acid is purified by maceration with alcoholic solvent, preferably isopropanol.

In another embodiment, the pure 3β-acetoxy betulinic acid is treated with aqueous-alcoholic alkaline solution, preferably aqueous methanolic sodium hydroxide or potassium hydroxide, to give pure betulinic acid (β-isomer).

In still another embodiment, betulinic acid is isolated by filtration or centrifugation.

In a further embodiment, the preferred part of plant is bark.

The present invention provides a novel process for the isolation of betulinic acid having anticancer activity and also a base molecule for the synthesis of other new anticancer analogues produced by the applicants (accepted U.S. application Ser. No. 09/040,856 filed on Mar. 18, 1998).

In another feature, purification of 3β-acetoxy betulinic acid is selected from methanol, ethanol or isopropanol.

In another feature, deacylation of 3β-acetoxy betulinic acid is carried out using alcoholic aqueous sodium or potassium hydroxide to get pure betulinic acid.

The process illustrated above for isolation of betulinic acid does not involve any chromatography at any stage.

In another feature, the process illustrated gives quantitative recovery of betulinic acid from the raw material used.
The Preferred Process Comprises the Following Steps
1) The bark of *Ziziphus jujuba* is pulverized and may be optionally dried. Aromatic hydrocarbon solvents selected from benzene, toluene or xylene is added to ground bark and the mixture stirred at approximately 90–95° C. for 12 hours. The preferred aromatic hydrocarbon used in the present process is toluene.
2) The semi concentrated extract so obtained contains betulinic acid and other chemical compounds. This is chilled between 0° C.–10° C. for 16–24 hours. The insoluble material containing betulinic acid is then separated out by filtration or centrifugation. The mother liquor left behind is discarded.
3) The solid of step(2) is dissolved in hot methanol and refluxed with activated charcoal for an hour and filtered through a celite bed. The clear mother liquor was concentrated to a reduced volume and methylene chloride was added and the solution chilled to 0–10° C. for 16–24 hours. The solid is separated by filtration or centrifugation which constituted crude betulinic acid.
4) Solid of step(3) is dissolved in methylene chloride containing few drops of dry pyrdine and treated with acetic anhydride or acetyl chloride. The mixture is stirred at room temperature overnight and worked-up by pouring on to crushed ice with stirring, the organic layer is then separated, washed with dilute acid, aqueous bicarbonate solution, followed by water. The organic layer is dried over anhydrous sodium sulphate, evaporated to dryness to yield crude 3β-acetoxy betulinic acid.
5) The solid of step (4) is washed with isopropanol at room temperature and filtered to separate the solid which constitutes pure 3β-acetoxy betulinic acid.
6) Solid of step (5) is dissolved in methanol and treated with aqueous alkali selected from sodium or potassium hydroxide. The mixture is stirred for 16–24 hours at room temperature. This is evaporated completely methanol under reduced pressure (100–150 mbar), followed by water, and the pH is adjusted to 7.0 by addition of aqueous dilute hydrochloric acid. The solid obtained is separated by filtration or centrifugation, washed with water to neutrality to yield pure betulinic acid.

The advantage of the above process is that it is cheap, simple, non-hazardous, ecofriendly and the solvents used in various steps can be recycled.

The above novel process is described in detail by the following examples, which are provided for illustrating only, and should not be construed to limit the scope of present invention.

EXAMPLE 1

The bark of *Ziziphus jujuba* optionally dried is finely pulverised (#100 mesh). An aromatic hydrocarbon extract is prepared by stirring 1200 Ltrs. of toluene (in 3 lots) with 100 kgs. of bark (rotation 58 rpm, ca.90–95° C.) for 12 hours each time. The toluene solution collected after filtration or centrifugation is concentrated ca. 60–70° C. under reduced pressure (150 mbar) to one fiftieth of its original volume, chilled to 0–10° C. for a period of 16–24 hours. The solid is separated by filtration or centrifugation, washed with toluene (500 ml) to yield a brown solid (1210 gms).

Dried brown solid (1210 gms) is dissolved in reflux methanol (110 ltrs) and treated with activated charcoal (60 gms) and the mixture is stirred at reflux temperature for an hour. The methanolic solution is filtered through celite bed and the clear solution obtained is obtained partially concentrated to reduce the volume to 2.4 ltrs. To this halogenated solvent (preferably methylene chloride) 600 ml is added which provides a ratio of 1:4 (methanol to methylene chloride), and the solution is chilled 0° C. to 5° C. overnight. The insoluble material is removed by filtration or centrifugation to get a solid enriched in betulinic acid (720 gms).

EXAMPLE 2

The enriched betulinic acid (720 gms) is dissolved in methylene chloride (7.5 ltrs) containing pyridine (250 ml) and added acetic anhydride (250 ml) and the mixture is stirred at room temperature for 16–24 hours. This is worked-up by washing the reaction mixture with dilute aqueous HCl, aqueous NaHCO$_3$ followed by water. The organic layer is dried over anhydrous sodium sulphate, filtered and filtrate evaporated to dryness to yield crude 3β-acetoxy betulinic acid (810 gms).

EXAMPLE 3

Crude 3β-acetoxy betulinic acid (810 gms) was treated with isopropanol (1250 ml) and stirred at room temperature for an hour. Solid separated from mother liquor by filtration or centrifugation, dried under vacuum to give pure 3β-acetoxy betulinic acid (755 gms).

EXAMPLE 4

Pure 3β-acetoxy betulinic acid (755 gms) is dissolved in methanol (720 ml) and added 20% aqueous sodium hydroxide solution (145 ml) to adjust the pH to 9.0–10.0. Stirred the mixture at room temperature for 16–24 hours. Removed methanol completely under reduced pressure. Added water (400 ml) and adjusted the pH to 7.0 with aqueous 2N HCl. Solid separated by filtration or centrifugation, washed with water to neutrality and dried under vacuum ca 80° C. for 10–12 hours. The white solid obtained was pure betulinic acid (β-isomer; 690 gms) identified by spectral data. The betulinic acid obtained has about 98% purity.
Advantages of the Novel Process
a) It is simple, cost effective and has commercial feasibility.
b) It does not involve tedious process of chromatographic technique at any stage of this process.

c) In this process, there is reusability of the solvent in many steps.
d) Depending on the quality of raw material which is dependent on seasonal collection, the yield of betulinic acid varies from 0.3 to 0.7 w/w % of the plant material.
e) In this process, there is quantitative recovery of betulinic acid from the plant material used

What is claimed is:

1. A process for isolating betulinic acid from *Ziziphus jujuba,* comprising the steps of:
   a) extracting bark of *Ziziphus jujuba* in a solvent to obtain an extract containing betulinic acid,
   b) semi-concentrating the extract containing betulinic acid,
   c) chilling said semi-concentrated extract overnight to obtain a solid in the extract,
   d) separating the solid from the extract by filtration or centrifugation,
   e) dissolving the separated solid from step d) in hot methanol, refluxing with activated charcoal and filtering through a celite bed to obtain a methanolic solution,
   f) partially concentrating the methanolic solution of step e), adding halogenated hydrocarbon solvent and chilling overnight to obtain a solid in the solution,
   g) separating the solid of step f) by filtration or centrifugation and drying the solid to obtain a solid enriched in betulinic acid,
   h) dissolving the dried solid of step g) in a solvent containing pyridine and acetic anhydride, separating an organic layer and drying to obtain a crude solid 3-acetoxy betulinic acid,
   i) washing the crude solid 3-acetoxy betulinic acid obtained in step h) with an alcohol to yield pure solid 3-acetoxy betulinic acid, and
   j) dissolving the pure solid 3-acetoxy betulinic acid obtained in step i) in an aqueous alcoholic alkali solution to yield pure betulinic acid.

2. The process of claim 1, wherein said solvent used in extracting the bark of *Ziziphus jujuba* is selected from the group consisting of benzene, toluene and xylene.

3. The process of claim 1, wherein said solvent used in extracting the bark of *Ziziphus jujuba* is toluene.

4. The process of claim 1, wherein the halogenated hydrocarbon solvent is methylene chloride.

5. The process of claim 1, wherein the alcohol for washing in step i) is selected from the group consisting of methanol, ethanol, and isopropanol.

6. The process of claim 1, wherein chilling in step c) is at a temperature between 0° C. to 10° C.

7. The process of claim 1, wherein in step f) the partially concentrating is under reduced pressure and the chilling is performed between 0° C. to 10° C.

8. The process of claim 1, wherein the alcohol in step i) is isopropanol.

9. The process of claim 1, wherein in step f) the halogenated hydrocarbon methylene chloride and the solid is formed by crystallization during said chilling.

10. The process of claim 1, wherein the alcoholic alkali is methanolic sodium hydroxide or methanolic potassium hydroxide.

11. The process of claim 1, wherein in step j) the pure betulinic acid is isolated from the solution by filtration or centrifugation.

12. The process of claim 1, wherein in step j) the pure betulinic acid has a purity greater than 98%.

13. The process of claim 1, wherein the halogenated hydrocarbon solvent in step f), is methylene chloride and the amount of methylene chloride to the amount of methanol is in a ratio of 1:4, respectively.

* * * * *